United States Patent [19]

Hansen et al.

[11] Patent Number: 5,499,721
[45] Date of Patent: Mar. 19, 1996

[54] SUPPLY STAND CLAMP

[75] Inventors: Anlynne M. Hansen, Fremont, Ohio; Herschel Anderson, Kansas City, Mo.

[73] Assignee: Schroer Manufacturing Company, Kansas City, Mo.

[21] Appl. No.: 283,283

[22] Filed: Jul. 29, 1994

[51] Int. Cl.$^6$ ........................................... A47F 5/00
[52] U.S. Cl. .............. 211/13; 211/60.1; 211/113; 248/316.2; 248/412; 5/658; 403/261; 403/373
[58] Field of Search .............. 211/13, 60.1, 113; 248/316.1, 316.2, 231, 230, 411, 412; 5/658; 403/261, 373, DIG. 4

[56] References Cited

U.S. PATENT DOCUMENTS

| | | |
|---|---|---|
| 3,337,880 | 8/1967 | Florek . |
| 3,709,372 | 1/1973 | Alexander . |
| 4,489,454 | 12/1984 | Thompson . |
| 4,511,158 | 4/1985 | Varga et al. . |
| 4,523,683 | 6/1985 | Fullenkamp et al. . |
| 4,572,536 | 2/1986 | Doughty . |
| 4,689,043 | 8/1987 | Bisha . |
| 4,706,368 | 11/1987 | Crissman, III et al. . |
| 4,767,131 | 8/1988 | Springer et al. ................. 248/316.2 X |
| 4,832,299 | 5/1989 | Gorton . |
| 4,886,237 | 12/1989 | Dennis . |
| 4,905,944 | 3/1990 | Jost et al. . |
| 4,919,654 | 4/1990 | Kalt . |
| 4,966,590 | 10/1990 | Kalt . |
| 5,078,349 | 1/1992 | Smith .................................. 248/412 X |
| 5,094,418 | 3/1992 | McBarnes et al. ....................... 5/658 X |
| 5,149,030 | 9/1992 | Cockrill . |
| 5,149,036 | 9/1992 | Sheehan . |
| 5,161,764 | 11/1992 | Roney . |
| 5,171,301 | 12/1992 | Vanderveen . |
| 5,228,796 | 7/1993 | Kao .................................. 248/316.2 X |
| 5,236,162 | 8/1993 | Desjardins . |

Primary Examiner—Robert W. Gibson, Jr.
Attorney, Agent, or Firm—Stinson, Mag & Fizzell

[57] ABSTRACT

A device and method for securing at least one, and normally a plurality of supply stands in one localized area of a patient table. The device generally comprises a mounting means for removably attaching the device to the patient table and a clamping means for removably clamping the post of the supply stand to the device. The clamping means comprises a restraining member having at least one opening and a shiftable cylinder proximate to the opening in the restraining member for receiving and rigidly maintaining the post of the supply stand perpendicularly to the patient table.

19 Claims, 5 Drawing Sheets fig.1

SUPPLY STAND CLAMP

FIELD OF THE INVENTION

The invention relates to a device and method for securing at least one, and normally a plurality of supply stands in one localized area of a patient table.

BACKGROUND OF THE INVENTION

The development of new medical techniques and methods has caused an increase in the number of items attached to the patient table. For example, a patient with a chest wound or heart problem may require several IVs delivering drugs, blood and food intravenously to the patient. The patient may also require a heart monitor, a breathing monitor and other devices that must be transported when the patient is moved. Other medical problems require that infusion pumps, suction apparatus, blood pressure monitors, syringe pumps and other medical equipment also be attached to the patient table.

Figure 1:
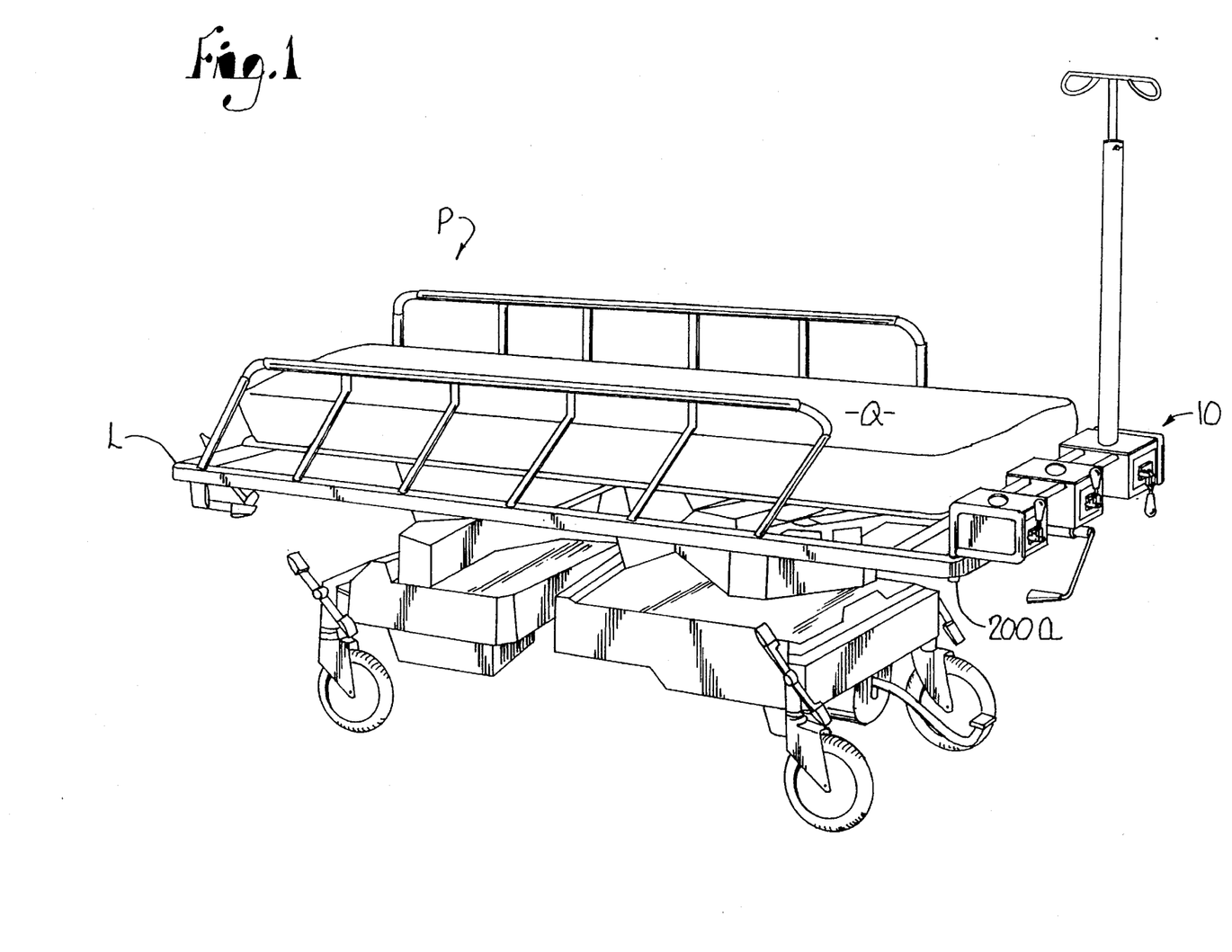
FIG. 1 is a perspective view of the preferred embodiment attached to the foot of a patient table with the patient support surface in the standby position.

Current day patient tables, i.e. emergency gurneys, hospital beds and surgical tables, attempt to address the need for multiple IVs and accessible monitors and other apparatus by attaching receiving shafts to the corners of the patient table (see FIG. 1). These shafts currently allow attachment of single unit IV stands. The post of the single unit IV stand slides into the shaft and is maintained in place by the shaft being closed on the bottom.

This current practice is clumsy and oftentimes medically undesirable. To reach the single unit IV stands, the care provider must physically move to each corner of the patient table. In many instances, this required movement is not possible. For example, if the care provider is administering oxygen, she must remain near the patient's head. With this limited range of movement, IV stands at the patient's feet are unaccessible. Consequently, an additional care provider is required to access the IV stands at the patient's feet. Due to the increased demand for supply stands that attach to the patient table, yet are accessible by only one care provider, a need exists for a device which allows localized attachment of a plurality of supply stands.

SUMMARY OF THE INVENTION

The invention relates to a device and method of using the same for securing at least one, and normally a plurality of supply stands in one localized area of a patient table. The device comprises a mounting means for removably attaching the device to a patient table and a clamping means attached to the mounting means for removably clamping the supply stands to the device.

The clamping means is comprised of a restraining member having an opening for accepting the post of the supply stand perpendicularly to the patient support surface of the patient table. The opening in the restraining member is generally proximate to a shiftable cylinder. The shiftable cylinder may be oriented in a first position or a second position dependent on whether the clamping means is in use. A retracting rod attached to a manually operated handle is used to manually shift the shiftable cylinder from its first position to its second position.

The first position of the shiftable cylinder is such that the shiftable cylinder communicates with the opening of the restraining member, allowing the post of the supply stand to be simultaneously inserted into the opening of the restraining member and the shiftable cylinder. The second position of the shiftable cylinder is such that the post is rigidly secured by the shiftable cylinder, the opening in the restraining member and the retracting rod.

The restraining member of applicants' device is generally comprised of a top panel, bottom panel, front panel and back panel. The opening is comprised of an orifice in the top panel and an orifice in the bottom panel. The orifices are aligned such that the post of the supply stand passes through the housing perpendicular to the patient support surface in the standby position.

In one embodiment, multiple housings exist with each housing having an interior front panel and interior back panel. The opening is located between the two interior panels. The shiftable cylinder is also located between the two interior panels. In an alternative embodiment, only one housing exists with multiple openings. A bracket is attached to the interior side of the top panel of the housing. The upper portion of the shiftable cylinders fits into this bracket for maintaining the shiftable cylinders proximate to the openings.

Applicants' invention also includes two embodiments of the mounting means. Version one consists of at least one leg attached to the clamping means for insertion into the receiving shaft of the patient table. Version two has a bracket attached to the clamping means for engaging the longitudinal support surface of the patient table.

DETAILED DESCRIPTION OF TEE PREFERRED EMBODIMENT

Figure 2:
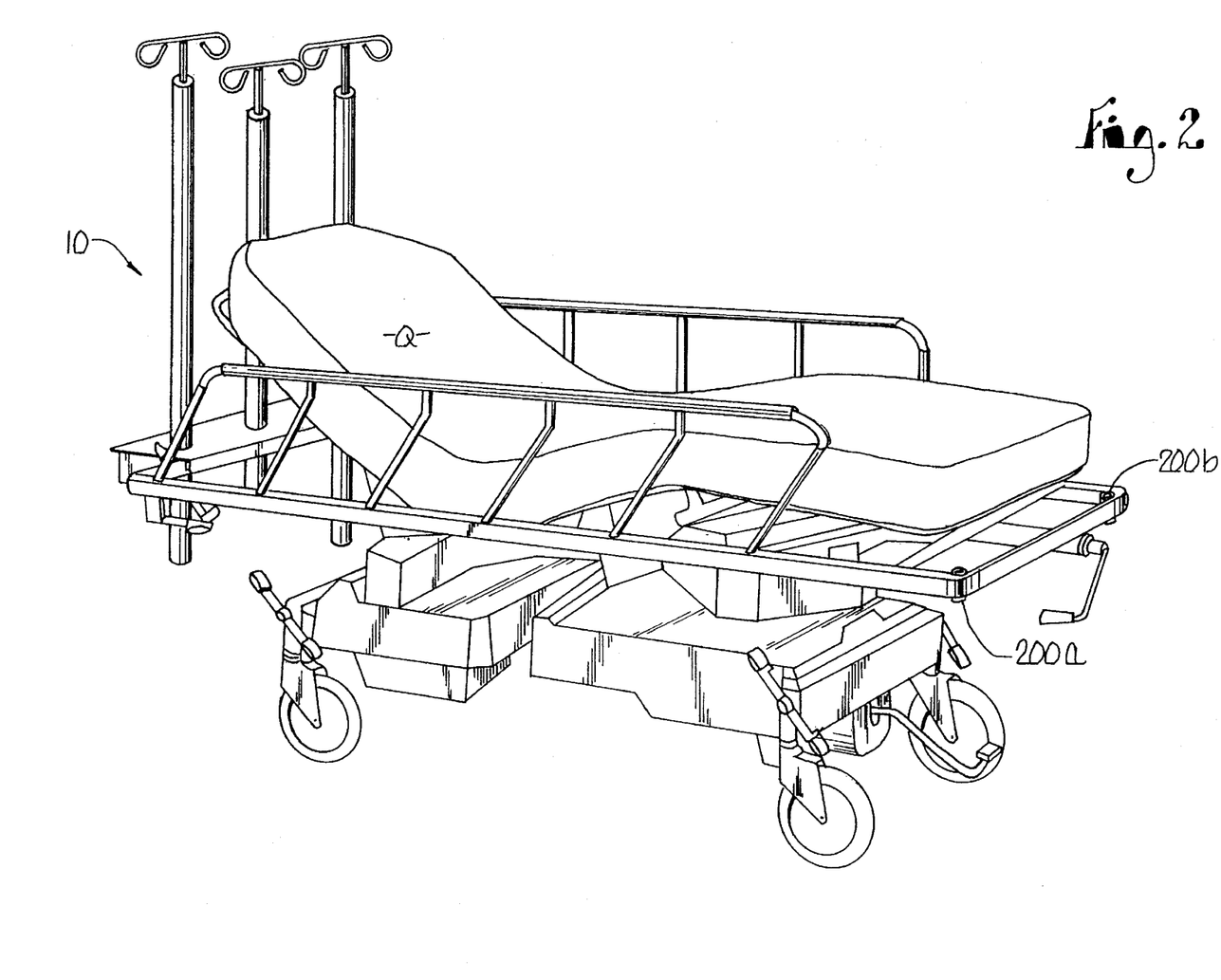
FIG. 2 is a perspective view of one alternative embodiment attached to the head of a patient table.

FIG. 1 is a perspective view of the preferred embodiment of supply stand clamp 10 attached to patient table P via shafts 200a and 200b (see FIG. 2). Patient table P of FIG. 1 is in the standby position. FIG. 2 is a perspective view of an alternative embodiment of supply stand clamp 10' with supply stand clamp 10' attached to longitudinal support surface L at the head of patient table P. In either embodiment, supply stand clamp 10 or 10' is constructed of materials that are capable of being sterilized, for example, stainless steel, aluminum and hard plastics with the preferred being stainless steel.

Figures 3, 4:
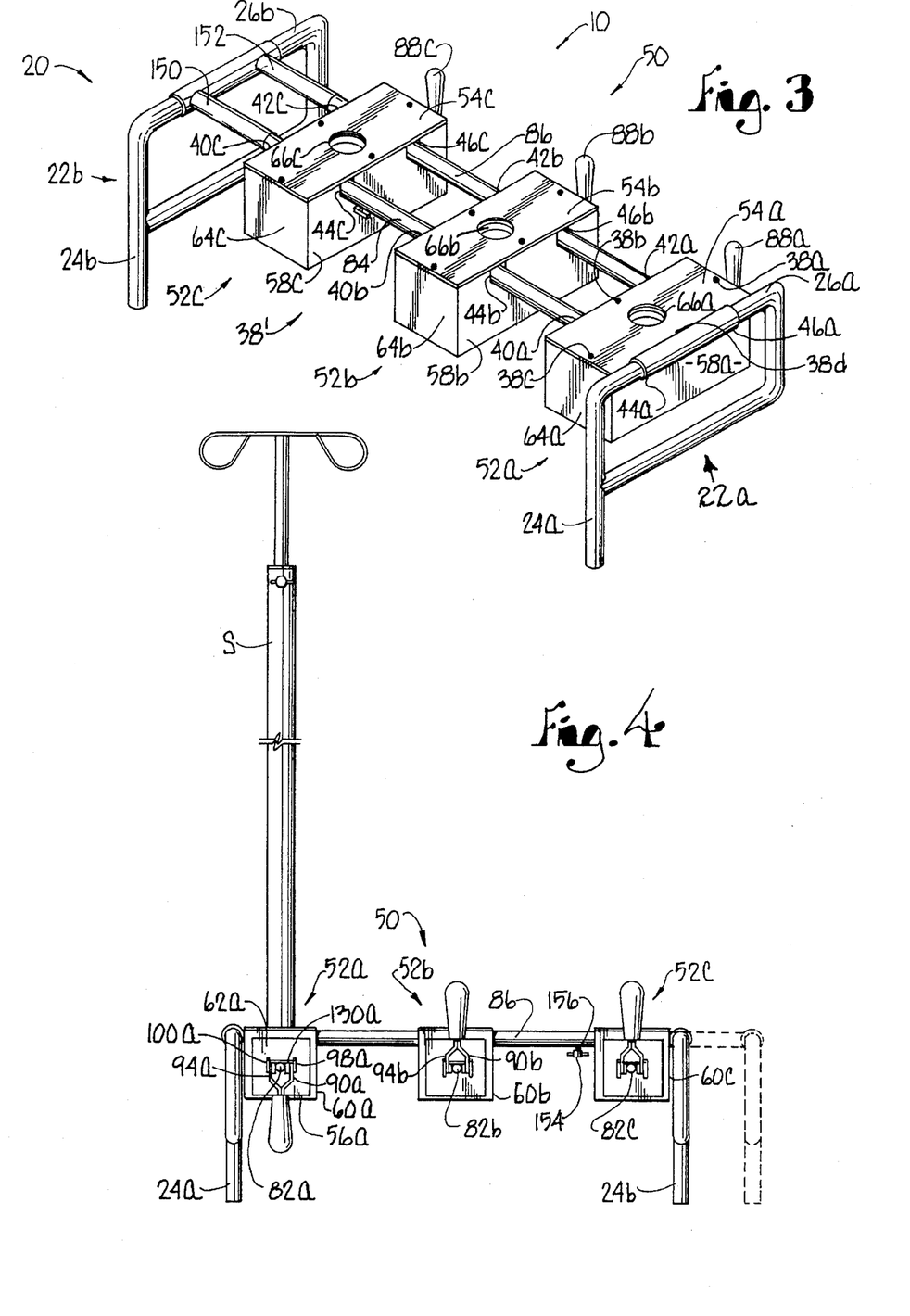
FIG. 3 is a perspective view of the preferred embodiment with all clamping means available for use.
FIG. 4 is a side view of the preferred embodiment with one clamping means in use and the telescoping capability of the mounting means illustrated.

Referring to FIGS. 3 and 4, supply stand clamp 10 is comprised of mounting means 20 and clamping means 50. Mounting means 20 is comprised of support members 22a and 22b. Support member 22a is comprised of leg 24a translating into attaching arm 26a. Support member 22b is comprised of leg 24b translating into attaching arm 26b. In use, leg 24a fits into receiving shaft 200a and leg 24b fits into receiving shaft 200b (see FIG. 1).

The preferred embodiment, as illustrated in FIG. 3, has clamping means 50 comprised of restraining member 38 which is comprised of housings 52a, 52b and 52c. In alternative embodiments of the preferred embodiment, fewer or additional housings could be used dependent upon the number of supply stands required.

Housing 52a is comprised of top panel 54a, bottom panel 56a, side panel 58a, side panel 60a, front panel 62a and back panel 64a. Top panel 54a, has first orifice 66a. Bottom panel 56a has second orifice 68a (see FIG. 6). First orifice 66a and second orifice 68a are aligned such that the post of supply stand S passes through both first orifice 66a and second orifice 68a such that the position of supply stand S is perpendicular to patient support surface Q in the standby position as shown in FIG. 1. Second orifice 68a allows the post of supply stand S to pass through housing 52a such that the height of supply stand S may be adjusted.

Figure 6:
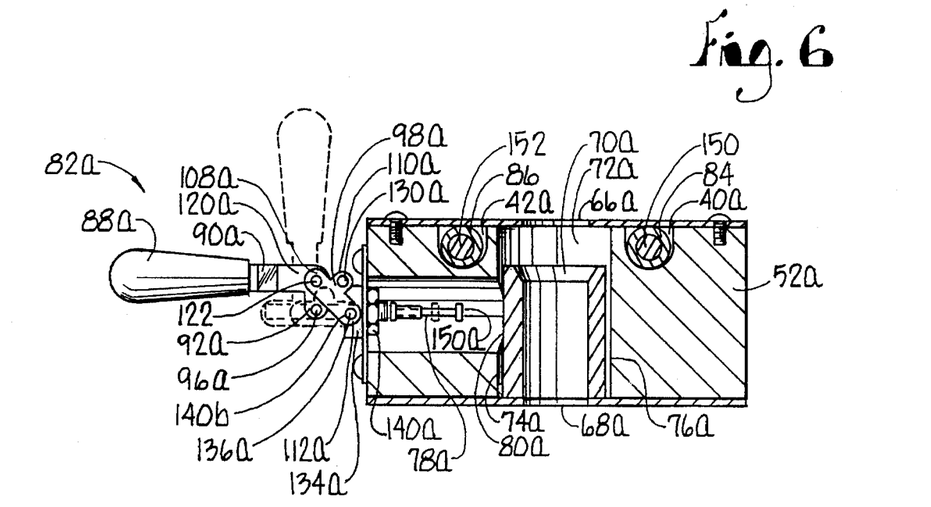
FIG. 6 is a cutaway side view of the preferred embodiment. The dotted lines illustrate the clamping means available for use.

Referring to FIG. 6, shiftable cylinder 70a is located within housing 52a. Shiftable cylinder 70a in FIG. 6 is in its first position. In the first position, shiftable cylinder 70a communicates with first orifice 66a and second orifice 68a such that the post of supply stand S inserts into first orifice 66a, enters shiftable cylinder 70a and exits through second orifice 68a. When supply stand S is locked in place, shiftable cylinder 70a is in its second position which is discussed below.

In the preferred embodiment as shown in FIGS. 3, 4 and 6, housing 52a may either be solid wherein bore 72a runs from first orifice 66a to second orifice 68a. Alternatively, if housing 72a is not solid, bore 72a may be created by the addition of interior front panel 74a and interior back panel 76a. Interior front panel 74a and interior back panel 76a are utilized to decrease the area of movement available to shiftable cylinder 70a. By decreasing the area of movement available to shiftable cylinder 70a, the placement of the post of supply stand S into shiftable cylinder 70a will be easier and quicker as shiftable cylinder will be adjacent first orifice 68a, and consequently, easily accessible without first stopping to align shiftable cylinder 70a with first orifice 66a.

Top panel 54, bottom panel 56, side panel 58, side panel 60, front panel 62 and back panel 64 are rigidly connected with screws, pins or welded or, if housing 52a is solid, bottom panel 56, side panel 58, side panel 60 and back panel 64 are machine tooled as one piece and top panel is attached with screws 38a–l as shown in FIG. 3. If interior front panel 74 and interior back panel 76 are utilized, they are connected by screws, pins or welding dependent on the type of material utilized.

In the second position, shiftable cylinder 70a is moved toward interior back panel 76a by retracting rod 78a via opening 80a in interior front panel 74a. Retracting rod 78a forces shiftable cylinder 70a towards interior back panel 76a and consequently causes the post of supply stand S to be wedged and held frictionally by the combination of retracting rod 78a, first orifice 66a, second orifice 68a, interior back panel 76a, interior front panel 74a and shiftable cylinder 70a.

Retracting rod 78a is attached to manually operable handle 82a. In FIG. 4, manually operable handle 82a is in the down position such that retracting rod 78a is fully extended against shiftable cylinder 70a. Consequently, in FIG. 4, shiftable cylinder 70a is in the second-position. In FIG. 6, the dotted lines illustrate manually operable handle 82a in the up position. In the up position, retracting rod 78a is fully withdrawn away from shiftable cylinder 70a.

Referring to FIG. 6, manually operable handle 82a is comprised of hand grasping segment 88a covering connecting arm 90a with offset end 92a and connecting arm 94a (see FIG. 4) with a similar offset end not shown. Offset end 92a of connecting arm 90a and the offset end of connecting arm 94a are connected to retracting rod 78a by pin 96a and a rivet not shown. Pin 96a goes through offset end 92a of connecting arm 94a, through retracting rod 78a, through the offset end of connecting arm 94a and is maintained in place by a rivet.

Manually operable handle 82a is capable of achieving both the up and down position via extenders 98a and 100a (see FIG. 4). Referring to FIG. 6, extender 98a is comprised of first arm 108a, second arm 110a and third arm 112a. Extender 100a is comprised of similar first arm, second arm and third arm. First arm 108a of extender 98a is connected to upper portion 120a of offset arm 92a of connecting arm 90a by pin 122a and a rivet not shown. The first arm of extender 100a is attached to connecting arm 94a in a similar fashion.

Extender 98a is connected to extender 100a by pin 130a and a rivet not shown. Manually operable handle 82a is attached to housing 52a by third arm 112a of extender 98a being connected to bolt 134a by pin 163a and a rivet not shown. A similar connection attaches the third arm of extender 100a to the other side of bolt 134a. Bolt 134a is maintained in place by nut 140a. Retracting rod 78a extends through orifice 140a in bolt area 134a. Retracting rod 78a is capped with cap 150a.

Housings 52b and 52c are similarly constructed as described in reference to housing 52a.

Referring to FIG. 4, housing 52a is connected to housings 52b and 52c via outer tubular body 84 and outer tubular body 86. Outer tubular bodies 84 and 86 are welded to attaching arms 26a and 26b. Outer tubular bodies 84 and 86 enter and exit housings 52a–c via openings 46a–c and 44a–c in side panel 58a–c and openings 40a–c and 42a–c in side panels 60a–c. Outer tubular bodies 84 and 86 are rigidly maintained in place by the force between top panels 54a–c and openings 46a–c, 44a–c, 42a–c and 40a–c.

Located within outer tubular body 84 is inner cylindrical body 150. Located within outer tubular body 86 is inner cylindrical body 152. Cylindrical bodies 150 and 152 are welded to attaching arm 26b. Outer tubular bodies 84 and 86, in conjunction with inner cylindrical bodies 150 and 152, causes mounting means 20 to be telescoping, allowing applicants' invention to be attached to variable size beds that have receiving shafts 200a and 200b at variable distances. Screw 154 frictionally engages inner cylindrical body 152 via threaded orifice 156 in outer tubular body 86 to assist in maintaining mounting means 20 at the desired length.

In an alternative embodiment, outer tubular bodies 84 and 86 and inner cylindrical bodies 150 and 152 could be secured to attaching arms 26a and 26b by screws, pins or other similar attaching methods.

Figure 5:
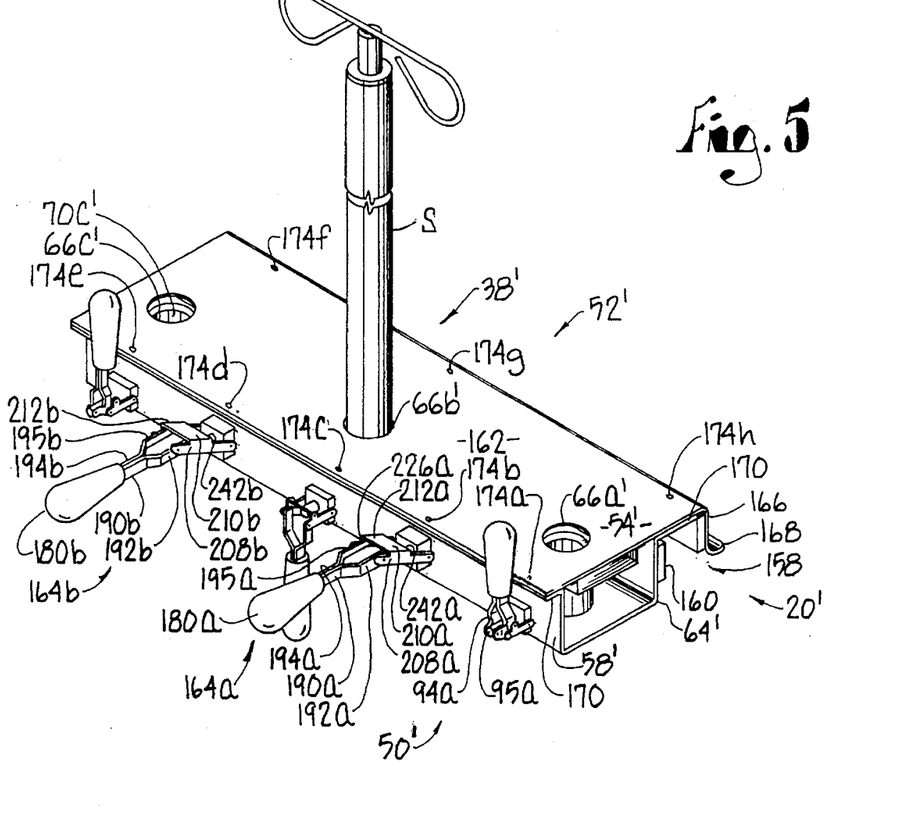
FIG. 5 is a top perspective view of an alternative embodiment with one clamping means in use and the adjustable securing bar open to its full extent.
Figure 7:
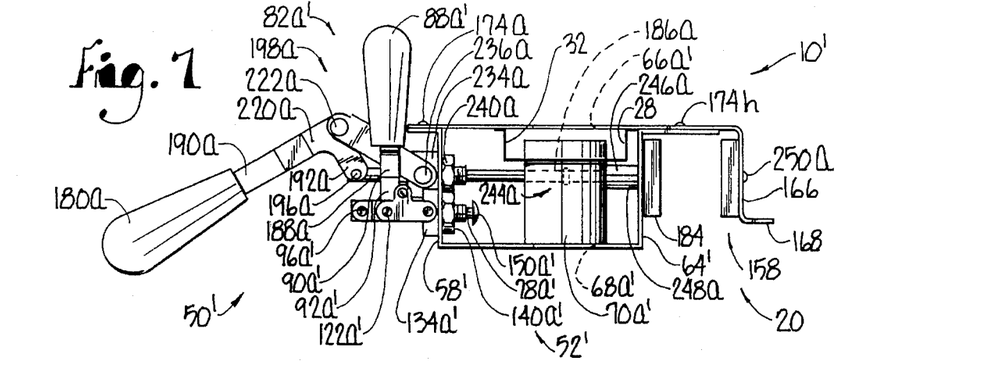
FIG. 7 is a cutaway side view of an alternative embodiment with the clamping means available for use and the adjustable securing bar not extended.
Figure 8:
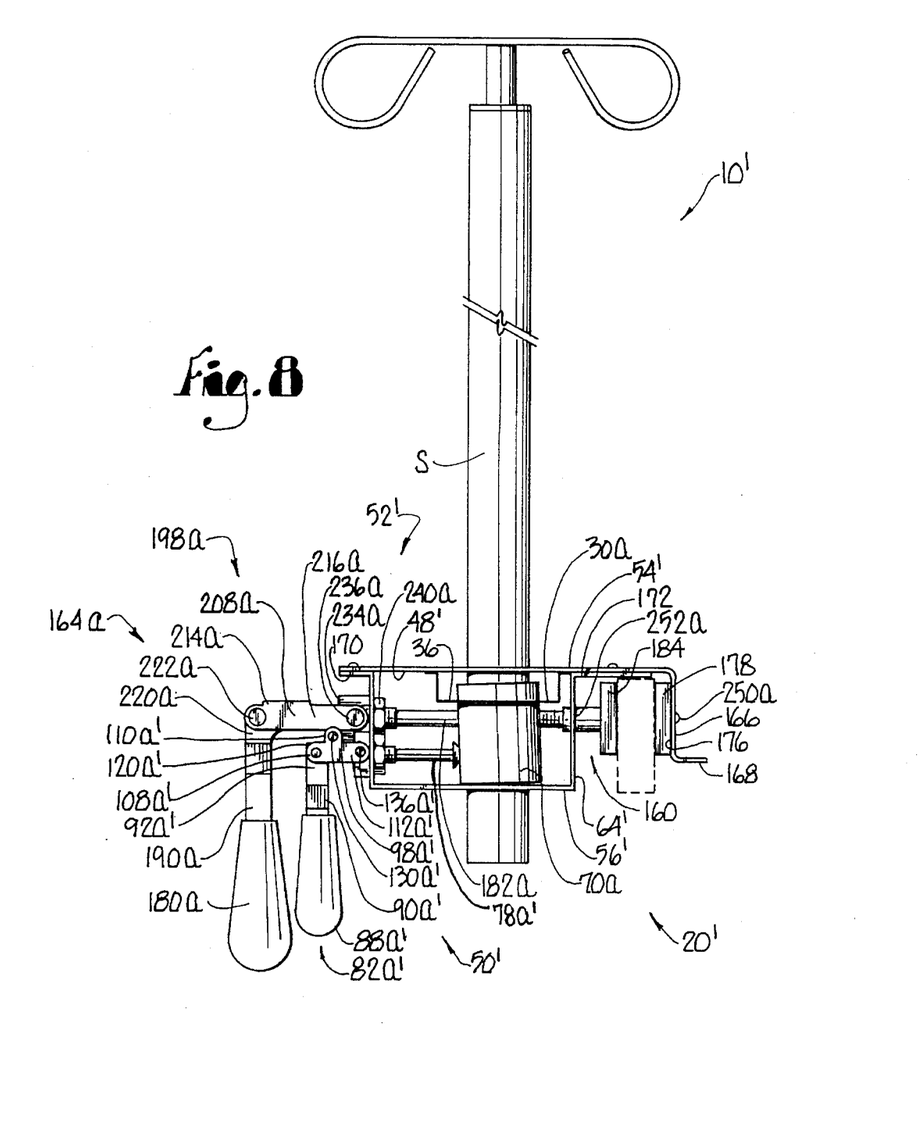
FIG. 8 is a cutaway side view of the alternative embodiment with the clamping means in use and the adjustable securing bar fully extended and in use.

FIGS. 2, 5, 7 and 8 illustrate an alternative embodiment, supply stand clamp 10'. Referring to FIGS. 5, 7 and 8, supply stand clamp 10' is comprised of mounting means 20' and clamping means 50'. Mounting means 20' is comprised of bracket member 158 with adjustable securing bar 160.

Adjustable securing bar 160 is manipulated by manually operable handles 164a and 164b.

As shown in FIGS. 5, 7 and 8, bracket member 158 is an extension of housing 52'. Alternative embodiments include a separate bracket member rigidly attached to back panel 64' of housing 52'. In the embodiment shown, top panel 54' extends over back panel 64', curving downward at approximately a 90 degree angle towards bottom panel 56' and then curving approximately 90 degrees away from back panel 64' creating bracket member 158 with side panel 166 and lip 168.

Front panel 58' and back panel 64' are machine tooled as extensions of bottom panel 56'. In the embodiment shown in FIGS. 5, 7 and 8, both ends of bottom panel 56' curve upward approximately 90 degrees towards top panel 54' and then curve parallel to top panel 54' creating front panel 58' with attaching lip 170 and back panel 64' with attaching lip 172. Housing 52' is constructed by attaching top panel 54' to lip attaching lips 170 and 172 by screws 174a–h. Attached by three screws 250a (shown on FIGS. 7 and 8) to interior side 176 of side panel 166 is bracing bar 178. Bracing bar 178 adds strength and rigidity to side panel 166.

Manually operable handle 164a is comprised of hand grasping segment 180a covering connecting arm 190a with offset end 192a and connecting arm 194a with offset end 195a. Offset end 192a of connecting arm 190a and offset end 195a of connecting arm 194a are connected to first end 188a of retracting rod 182a of adjustable securing bar 160 by pin 196a and a rivet not shown. Pin 196a passes through offset end 192a of connecting arm 194a, through first end 188a of retracting rod 182a, through offset end 195a of connecting arm 194a and is maintained in place by a rivet.

Manually operable handle 164a is capable of achieving both the up and down positions via extender 198a. Extender 198a is comprised of first arm member 208a, mid-section 210a and second arm member 212a (FIG. 5). First end 214a of first arm member 208a of extender 198a is connected to upper portion 220a of offset arm 192a of connecting arm 190a by pin 222a and a rivet not shown. The first end of second arm member 212a of extender 198a is connected to upper portion 226a of offset end 195a of connecting arm 194a by pin 228a and a rivet 230a.

Manually operable handle 164a is attached to housing 52' by second end 216a of first arm member 208a of extender 198a being connected to bolt 234a by pin 236a and the second end of second arm member 212a of extender 198a being attached to bolt 234a by pin 236b. Bolt 234a is maintained in place by nut 240a. Retracting rod 182a extends through an orifice in bolt 234a.

Referring to FIG. 7, second end 186a of retracting rod 182a is attached to bolt 244a. Bolt 224a receives threaded nut 246a which attaches bar 184 to retracting rod 182a. Threaded spacer bolt 248a is attached to the end of threaded nut 246a opposite bolt 244a. Threaded spacer bolt 248a assists in assuring easy movement of bar 184 by sliding though orifice 252a in housing 52'.

Referring to FIG. 5, manually operable handle 164b is constructed in the same manner as discussed above in conjunction with manually operable handle 164a.

Housing 52' is comprised of top panel 54', bottom panel 56', front panel 62' and back panel 64'. Top panel 54' has first orifice 66a', first orifice 66b' and third orifice 66c'. Bottom panel 56' has second orifice 68a' (FIG. 7) and two other orifices not shown. First orifice 66a' and second orifice 68a' are aligned such that the post of supply stand S may pass through first orifice 66a' and second orifice 68a' in a position perpendicular to patient support surface Q in the standby position as shown in FIG. 1. Second orifice 68a' allows the post of supply stand S to pass through housing 52' such that the height of supply stand S may be adjusted. First orifice 66b' and third orifice 66c' are aligned similarly to the two orifices in bottom panel 56' that are not shown.

Within housing 52' is shiftable cylinder 70a' (see FIG. 7 and 8), 70c' and one additional shiftable cylinder not shown which is proximate to first orifice 66b'. Shiftable cylinder 70a' as shown in FIG. 7 is in its first position. In the first position, shiftable cylinder 70a' communicates with first orifice 66a' and second orifice 68a' such that the post of supply stand S inserts into first orifice 66a', enters shiftable cylinder 70a' and exits through second orifice 68a'. When supply stand S is locked in place, shiftable cylinder 70a' is in its second position which is discussed below.

In the embodiment shown in FIGS. 5, 7 and 8, welded to interior side 48' of top panel 54' of housing 52' is bracket means 28. Bracket means 28 is comprised of front panel 32, back panel 34 and bottom panel 36. Bottom panel 36 runs parallel to top panel 54 of housing 52'. Bottom panel 36 of bracket means 28 has first opening 30a and two additional openings similarly situated proximate to first orifice 66b' and first orifice 66c' not shown. Shiftable cylinder 70a' fits into first opening 30a of bottom panel 36 of bracket means 28. Shiftable cylinder 70c' fits into the third opening of bottom panel 36 of bracket means 28 which was not shown. The other shiftable cylinder not shown fits into the second opening of bottom panel 36 of bracket means 28 which was not shown. Bracket means 28 maintains shiftable cylinder 70a' in a position such that the post of supply stand S may be inserted into first orifice 66a', enter shiftable cylinder 70a' and exit through second orifice 68a' without the user spending unnecessary time attempting to align shiftable cylinder 70a' with first orifice 66a' and second orifice 68a'. Similar theory follows for the other shiftable cylinders.

In the second position, shiftable cylinder 70a' is moved toward back panel 34 of bracket means 28 by retracting rod 78a'. Retracting rod 78a' forces shiftable cylinder 70a' towards back panel 34 and consequently causes the post of supply stand S to be wedged and held frictionally by the combination of retracting rod 78a', first orifice 66a', second orifice 68a', back panel 34 and shiftable cylinder 70a'.

Retracting rod 78a' is attached to manually operable handle 82a'. In FIG. 8, manually operable handle 82a' is in the down position such that retracting rod 78a' is fully extended against shiftable cylinder 70a', meaning in FIG. 8, shiftable cylinder 70a' is in the second position. In FIG. 7, manually operable handle 82a' is in the up position. In the up position, retracting rod 78a' is fully withdrawn away from shiftable cylinder 70a'.

Referring to FIG. 7, manually operable handle 82a' is comprised of hand grasping segment 88a' covering connecting arm 90a' with offset end 92a' and connecting arm 94a' with offset end 95a' (see FIG. 5). Offset end 92a' of connecting arm 90a' and offset end 95a' of connecting arm 94a' are connected to retracting rod 78a' by pin 96a' and a rivet not shown. Pin 96a' goes through offset end 92a' of connecting arm 94a', through retracting rod 78a', through offset end 95a' of connecting arm 94a' and is maintained in place by a rivet.

Manually operable handle 82a' is capable of achieving both the up and down position via extenders 98a' and a second extender of similar structure on the other side of retracting 78a'. The second extender is connected similarly as discussed below in reference to extender 98a'. Extender 98a' is comprised of first arm 108a', second arm 110a' and third arm 112a'. First arm 108a' of extender 98a' is connected to upper portion 120a' of offset arm 92a' of connecting arm 90a' by pin 122a' and a rivet not shown. Extender 98a' is connected to the second extender by pin 130a' and a rivet not shown. Manually operable handle 82a' is attached to housing 52' by third arm 112a' of extender 98a' being connected to bolt 134a' by pin 136a'. Bolt 134a' is maintained in place by nut 140a'. Retracting rod 78a' extends through an orifice in bolt 134a' not shown. Retracting rod 78a' is capped with cap 150a'.

While certain forms of this invention have been illustrated and described herein, the invention is not limited thereto, except insofar as such limitations are included in the following claims.

What is claimed and desired to be secured as Letters Patent is as follows:

1. A device for securing at least one supply stand having a post to a patient table, said patient table having an adjustable patient support surface which in its standby position is generally parallel to a non-inclined floor, said device comprising:

a. mounting means for removably attaching said device to said patient table;

b. clamping means attached to said mounting means for removably clamping said supply stand to said device, said clamping means comprising:

i. a restraining member having at least one opening for receiving said post of said supply stand perpendicularly to said patient support surface in said standby position;

ii. a shiftable cylinder located proximate to said opening of said restraining member, said shiftable cylinder having a first position and a second position;

iii. a retracting rod for moving said shiftable cylinder from said first position to said second position; and iv. a manually operable handle attached to said retracting rod for manipulating said retracting rod;

aa. said first position of said shiftable cylinder being such that said shiftable cylinder communicates with said opening of said restraining member allowing said post of said supply stand to be simultaneously inserted into said opening of said restraining member and said shiftable cylinder; and bb. said second position of said shiftable cylinder being such that said post is rigidly secured by said shiftable cylinder, said opening of said restraining member and said retracting rod.

2. The device of claim 1 further comprising a plurality of clamping means.

3. The device of claim 2 wherein said restraining member is comprised of a plurality of housings, said housings each having an opening and a shiftable cylinder located within said housing proximate to said opening such that when said post of said supply stand is inserted in said opening and said shiftable cylinder, said post of said supply stand is perpendicular to said patient support surface in said standby position.

4. The device of claim 2 wherein said restraining member comprises a housing having a plurality of openings and a plurality of shiftable cylinders located within said housing proximate to said openings such that when said post of said supply stand is inserted in said opening and said shiftable cylinder, said post of said supply stand is perpendicular to said patient support surface in said standby position.

5. The device of claim 4 wherein said housing is comprised of a top panel, bottom panel, front panel and back panel;

said openings comprised of a first orifice in said top panel and a second orifice in said bottom panel, said first orifice and said second orifice being aligned such that said post of said supply stand passes through said housing perpendicularly to said patient support surface in said standby position.

6. The device of claim 5 wherein said top panel has an interior side and an exterior side; and a bracket means fixedly attached to said interior side of said top panel for maintaining said shiftable cylinders proximate to said first orifices in said top panel and said second orifices in said bottom panel.

7. The device of claim 3 wherein said housings are comprised of a top panel, bottom panel, front panel and back panel;

said openings comprised of a first orifice in said top panel and a second orifice in said bottom panel, said first orifice and said second orifice being aligned such that said post of said supply stand passes through said housing perpendicularly to said patient support surface in said standby position.

8. The device of claim 7 wherein said housings are further comprised of an interior front panel parallel to said front panel and an interior back panel parallel to said back panel;

said opening and said shiftable cylinder located between said interior front panel and said interior back panel.

9. The device of claim 1 wherein said patient table has a longitudinal support surface generally parallel to said patient support surface in said standby position, said mounting means comprising:

a bracket member attached to said clamping means for engaging said longitudinal support surface; and said bracket member having an adjustable securing bar for mounting said device to variable size longitudinal support surfaces.

10. The device of claim 9 wherein said adjustable securing bar is manipulated by at least one retracting rod attached to a manually operable handle.

11. The device of claim 1 wherein said patient table has at least one receiving shaft perpendicular to said patient support surface in said standby position, said mounting means comprising:

a first leg attached to said clamping means for insertion into said receiving shaft of said patient table.

12. The device of claim 11 wherein said patient table has at least two receiving shafts perpendicular to said patient support surface in said standby position, said mounting means further comprising:

an outer tubular body having a first end and a second end;

an inner cylindrical body having a first end and a second end;

said first end of said cylindrical body slidably telescopically insertable into said second end of said outer tubular body;

said outer tubular body attached to said clamping means;

said first leg attached to said first end of said outer tubular body; and a second leg attached to said second end of said inner cylindrical body for insertion into said second receiving shaft of said patient table.

13. The device of claim 3 wherein said patient table has at least one receiving shaft perpendicular to said patient support surface in said standby position, said mounting means comprising:

a first leg attached to one of said housings for insertion into said receiving shaft of said patient table.

14. The device of claim 13 wherein said patient table has at least two receiving shafts perpendicular to said patient support surface in said standby position, said mounting means further comprising:

an outer tubular body having a first end and a second end;

an inner cylindrical body having a first end and a second end;

said first end of said cylindrical body slidably telescopically insertable into said second end of said outer tubular body;

said outer tubular body attached to said housing;

said first leg attached to said first end of said outer tubular body; and a second leg attached to said second end of said inner cylindrical body for insertion into said second receiving shaft of said patient table.

15. The device of claim 4 wherein said patient table has a longitudinal support surface generally parallel to said patient support surface in said standby position, said mounting means comprising:

a bracket member attached to said housing for engaging said longitudinal support surface; and said bracket member having an adjustable securing bar for mounting said device to variable size longitudinal support surfaces.

16. The device of claim 15 wherein said adjustable securing bar is manipulated by at least one retracting rod attached to a manually graspable handle.

17. A method of securing at least one supply stand having a post to a patient table, said patient table having an adjustable patient support surface which in its standby position is generally parallel to a non-inclined floor, comprising the steps of:

a. mounting a device to said patient table, said device comprised of:

mounting means for removably attaching said device to said patient table;

at least one clamping means attached to said mounting means for removably clamping said supply stand as a device, said clamping means comprising:

a restraining member having at least one opening for receiving said post to said supply stand perpendicularly to said patient support surface and said stand-by position;

a shiftable cylinder located proximate to said opening of said restraining member, said shiftable cylinder having a first position and a second position;

a retracting rod for moving said shiftable cylinder from said first position to said second position; and a manually operable handle attached to said retracting rod for manipulating said retracting rod;

said first position of said shiftable cylinder being such that said shiftable cylinder communicates with said opening of said restraining member allowing said post to said supply stand to be simultaneously inserted into said opening and said shiftable cylinder;

said second position of said shiftable cylinder being such that said post is rigidly secured by said shiftable cylinder, said opening of said restraining member and said retracting rod;

b. inserting said post of said supply stand simultaneously in said opening and said shiftable cylinder; and c. rigidly securing said supply stand to said device by operating said manually operable handle to move said shiftable cylinder from said first position to said second position.

18. The method of claim 17, wherein said mounting means of said device further comprises a bracket member attached to said clamping means for engaging said longitudinal support surface, said bracket member having an adjustable securing bar for mounting said device to variable size longitudinal support surfaces, said method further comprising the steps of: attaching said bracket member to said longitudinal support surface.

19. The method of claim 17, wherein said patient table has at least one receiving shaft perpendicular to said patient support surface in said stand-by position, and said mounting means further comprising at least one leg attached to said clamping means for insertion into said receiving shaft of said patient table, further comprising the steps of:

inserting said leg into said receiving shaft of said patient table.

* * * * *